United States Patent
Riedrich et al.

(10) Patent No.: US 9,199,915 B2
(45) Date of Patent: Dec. 1, 2015

(54) PROCESS FOR PREPARING SUBSTITUTED BIPHENYLS BY C-H ACTIVATION

(71) Applicant: BAYER CROPSCIENCE AG, Monheim (DE)

(72) Inventors: Matthias Riedrich, Cologne (DE); Lars Rodefeld, Leverkusen (DE); Frank Volz, Cologne (DE)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 14/418,968

(22) PCT Filed: Jul. 29, 2013

(86) PCT No.: PCT/EP2013/065925
§ 371 (c)(1),
(2) Date: Feb. 2, 2015

(87) PCT Pub. No.: WO2014/019995
PCT Pub. Date: Feb. 6, 2014

(65) Prior Publication Data
US 2015/0203440 A1    Jul. 23, 2015

(30) Foreign Application Priority Data
Aug. 2, 2012 (EP) ..................... 12179058

(51) Int. Cl.
*C07C 231/12* (2006.01)
(52) U.S. Cl.
CPC ..................... *C07C 231/12* (2013.01)
(58) Field of Classification Search
None
See application file for complete search history.

(56) References Cited

PUBLICATIONS

Database CASREACT in STN, No. 150:422452, Li et al., Gaodeng Xuexiao Huaxue Xuebao (2008), 29(12), pp. 2535-2541 (reaction 20 of 28).*
Database CAPLUS in STN, Acc. No. 2009:7094, Li et al., Gaodeng Xuexiao Huaxue Xuebao (2008), 29(12), pp. 2535-2541 (abstract).*
Database CASREACT in STN, No. 132:347396, Jeong et al., Bulletin of the Korean Chemical Society (2000), 21(2), pp. 165-166 (reaction 9 of 12).*
Database CAPLUS in STN, Acc. No. 2000:182710, Jeong et al., Bulletin of the Korean Chemical Society (2000), 21(2), pp. 165-166 (abstract).*
Shabashov et al., Journal of Organic Chemistry (2007), 72(20), pp. 7720-7725.*
International Search Report dated Oct. 4, 2013, issued in counterpart International Application No. PCT/EP2013/065925.
Brasche et al., "Twofold C-H Functionalization: Palladium-Catalyzed Ortho Arylation of Anilides", Organic Letters. vol. 10, No. 11: 2207-2210. (2008).
Wencel-Delord et al., "Rhodium (III) and Hexabromobenzene—A Catalyst System for the Cross-Dehydrogenative Coupling of Simple Arenes and Heterocycles with Arenes Bearing Directing Group", Angewandte Chemie International Edition. vol. 51, No. 9: 2247-2251. (2012).
Li et al., "Multiple C-H Activations to Construct Biologically Active Molecules in a Process Completely Free of Organohalogen and Organometallic Components", Angewandte Chemie International Edition. XP55047422A. vol. 47, No. 6: 1115-1118. (2008).
Ashenhurst, James A., "Intermolecular oxidative cross-coupling of arenes" Chemical Society Reviews. vol. 39: 540-548. (2010).
You et al., "Palladium_catalyzed Aryl-Aryl Bond Formation Through Double C-H Activation", Top Curr Chem. vol. 292: 165-194. (2010).

* cited by examiner

*Primary Examiner* — Brian J Davis
(74) *Attorney, Agent, or Firm* — Miles and Stockbridge

(57) ABSTRACT

The present invention relates to a novel process for preparing substituted biphenyls of the formula (III) by reacting arenes of the formula (I) with arenes of the formula (II) in the presence of a transition metal catalyst and of at least one oxidizing agent. $R^1$ is $NO_2$, an amino or amide group or a Schiff base.

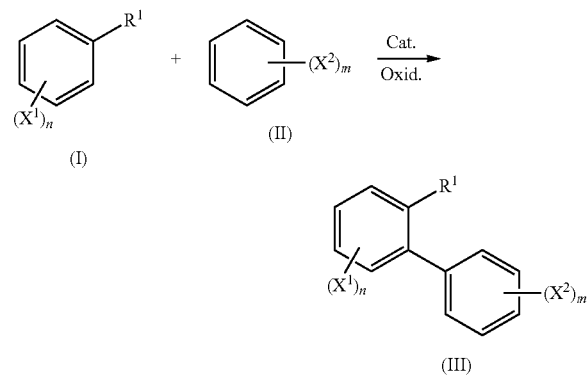

20 Claims, No Drawings

PROCESS FOR PREPARING SUBSTITUTED BIPHENYLS BY C-H ACTIVATION

CROSS REFERENCE TO RELATED APPLICATIONS

This application is a §371 National Stage Application of PCT/EP2013/065925, filed Jul. 29, 2013, which claims priority to EP 12179058.8, filed Aug. 2, 2012.

BACKGROUND

1. Field of the Invention

The present invention relates to a novel process for preparing substituted biphenyls of the formula (III) by reacting arenes of the formula (I) with arenes of the formula (II) in the presence of a transition metal catalyst and of at least one oxidizing agent.

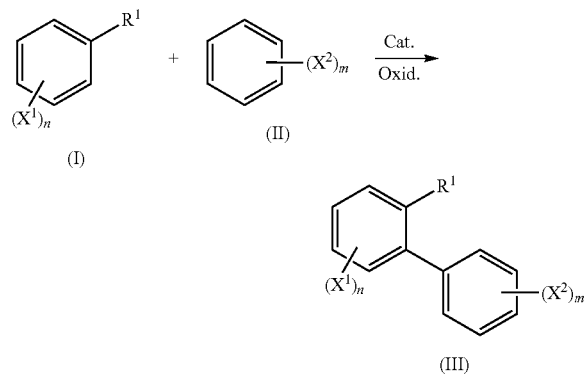

2. Description of Related Art

Biaryl compounds, especially biphenyl compounds, are of industrial significance as fine chemical is intermediates for pharmaceuticals, optical brighteners and agrochemicals.

It is known that substituted biphenyls are obtainable by Suzuki couplings. For this purpose, however, costly borinic/boronic acids with haloarenes are required as starting compounds, these being coupled to one another in the presence of a transition metal catalyst; cf. WO 2011/023324 A1. Recently, the synthesis of biphenyls by direct double C—H activation has been developed as an attractive alternative to the existing synthesis methods (e.g. Suzuki reaction). In this method, arenes bearing a directing group are reacted with arenes in the presence of transition metal catalysts and/or suitable activating reagents. Review articles on this topic can be found, for example, in Charles S. Yeung, Vy M. Dong, *Chem. Rev.* 2011, 111, 1215-1292. A review of Pd-catalysed aryl-aryl coupling by double C—H activation is given by Shu-Li You and Ji-Bao Xia, *Top. Curr. Chem.* 2010, 292, 165-194. A review of oxidative cross-couplings of arenes can be found in James A. Ashenhurst, *Chem. Soc. Rev.* 2010, 39, 540-548. The particular advantage of direct double C—H activation is the enhanced sustainability compared to the existing synthesis methods (e.g. Suzuki reaction). No pre-functionalized coupling partners are required, as a result of which the number of reaction steps and waste are reduced.

However, in this reaction type, there are also a multitude of difficulties, for example unfavourable thermodynamics, the generally low reactivity of C—H bonds and selectivity problems (functionalization of a C—H bond in the presence of other C—H bonds, and the competition between hetero and homo coupling). In the Pd-catalysed aryl-aryl couplings through double C—H activation described in the prior art, the descriptions by, for example, Gordon Brasche, Jorge García-Fortanet, Stephen L. Buchwald in *Org. Lett.* 2008, 10(11), 2207-2210 are restricted to the reaction of anilides with electron-rich arenes (containing electron-donating substituents such as Me, OMe, etc.). As well as the palladium catalyst, DMSO in combination with pure oxygen, and also TFA in combination with $Na_2S_2O_8$, are used here as additional activating reagents or oxidizing agents. Electron-poor aromatics (containing electron-withdrawing substituents such as F, $CF_3$, $CHF_2$, Cl, etc.) are considered too unreactive and can therefore be reacted with anilides under these reaction conditions only with very great difficulty, if at all.

Bi-Jie Li, Shi-Liang Tian, Zhao Fang, and Zhang-lie Shi, in *Angew. Chem.*, 2008, 47, 1115-1118, disclose processes with multiple C—H activation for preparation of biologically active molecules, the process being free of organohalogen and organometallic compounds. For example, a process for palladium-catalysed ortho-arylation of acetanilide with ortho-xylene using $O_2$ as an oxidizing agent and PrOH as a solvent is disclosed (Tab. 1, No. 6). Also disclosed is the coupling of an electron-poor arene (fluorobenzene) with N-acetyltetrahydroquinoline (Tab. 2, No. 8). However, a significantly higher amount of catalyst was required for this, the reaction was not stereoselective and the yield was only 48%.

Joanna Wencel-Delord, Corinna Nimphius, Frederic W. Patureau and Frank Glorius describe, in *Angew. Chem. Int. Ed.* 2012, 51, 2247-2251, an Rh-catalysed dehydrogenating aryl-aryl coupling which allows the use of electron-poor aromatics. To date, however, these conversions by C—H activation have been performed only with benzamides as directing coupling partners. The additives or oxidizing agents used here have been PivOH and CsOPiv, and also $AgSbF_6$ and $Cu(OAc)_2$. The use of anilides in the reaction with electron-poor arenes (containing electron-withdrawing substituents, for example F, $CF_3$, $CHF_2$, Cl, etc) has not been possible to date in the processes previously described in the prior art.

SUMMARY

It is therefore an object of the present invention to provide a novel process for preparing electron-poor biphenyls, especially those substituted by a plurality of (2, 3 or 4) halogen atoms, which does not have the disadvantages of the known processes, in particular the need for uneconomic synthesis units such as the abovementioned reactants.

This object is achieved by a process for preparing substituted biphenyls of the formula (III)

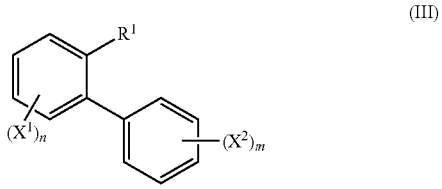

where
$X^1$ and $X^2$ are each independently selected from halogen atoms and linear or branched $C_{1-4}$-alkyl groups substituted by one or more halogen atoms;
n is selected from 0, 1 and 2;
m is selected from 1, 2, 3, 4 and 5;

$R^1$ is selected from the group consisting of —$NHR^2$, —$NO_2$, —$NR^3$—CO—$R^2$ and —N=$CR^4R^5$;

$R^2$-$R^5$ are selected from the group consisting of hydrogen, linear or branched $C_{1-12}$-alkyl groups, cyclic $C_{3-8}$-alkyl groups, —$CH_2$—CO—$CH_3$, benzyl groups, benzoyl groups, pyrazolyl groups of the formula (IVa) and pyridyl groups of the formula (IVb)

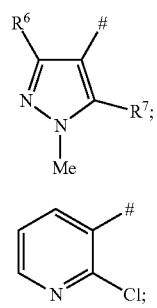

(IVa)

(IVb)

where, in the formulae (IVa) and (IVb), when $R^1$ is —$NR^3$—CO—$R^2$, the bond marked with # is bonded to the carbonyl group in each case, $R^6$ and $R^7$ are each selected from hydrogen, halogen, a linear or branched $C_{1-12}$-alkyl group and a $C_{1-6}$-haloalkyl group having 1 to 6 halogen atoms;

by reacting arenes of the formula (I)

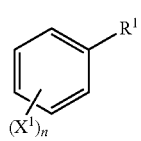

(I)

where
$R^1$, $X^1$ and n correspond to the above definitions with arenes of the formula (II)

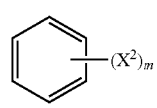

(II)

where
$X^2$ and m correspond to the above definitions,
the reaction being performed in the presence of a transition metal catalyst, of at least one oxidizing agent, up to ten, preferably up to five and more preferably up to three additives and in a solvent.

DETAILED DESCRIPTION OF A PREFERRED EMBODIMENT

In a preferred embodiment, this object is achieved by a process for preparing substituted biphenyls of the formula (III)

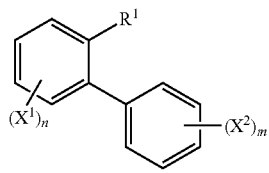

(III)

where
$X^1$ and $X^2$ are each independently selected from halogen atoms;
n is selected from 0, 1 and 2;
m is selected from 1, 2, 3, 4 and 5;
$R^1$ is selected from the group consisting of —$NHR^2$, —$NO_2$, —$NR^3$—CO—$R^2$ and —N=$CR^4R^5$;
$R^2$-$R^5$ are selected from the group consisting of hydrogen, linear or branched $C_{1-12}$-alkyl groups, cyclic $C_{3-8}$-alkyl groups, —$CH_2$—CO—$CH_3$, benzyl groups, benzoyl groups, pyrazolyl groups of the formula (IVa) and pyridyl groups of the formula (IVb)

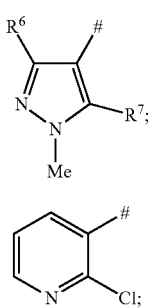

(IVa)

(IVb)

where, in the formulae (IVa) and (IVb), when $R^1$ is —$NR^3$—CO—$R^2$, the bond marked with # is bonded to the carbonyl group in each case,
$R^6$ and $R^7$ are each selected from hydrogen, halogen, a linear or branched $C_{1-12}$-alkyl group and a $C_{1-6}$-haloalkyl group having 1 to 6 halogen atoms;
by reacting arenes of the formula (I)

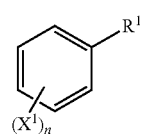

(I)

where
$R^1$, $X^1$ and n correspond to the above definitions with arenes of the formula (II)

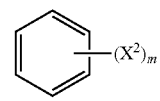

(II)

where
$X^2$ and m correspond to the above definitions, the reaction being performed in the presence of a transition metal catalyst, of at least one oxidizing agent, up to ten, preferably up to five and more preferably up to three additives and in a solvent.

This way of achieving the object of the invention is surprising with respect to the prior art. For instance, Joanna Wencel-Delord et al., *Angew. Chem. Int. Ed.* 2012, 51, 2247-2251 describe an Rh-catalysed dehydrogenating aryl-aryl coupling which permits the use of electron-poor aromatics. To date, however, these conversions by C—H activation have been performed only with benzamides as directing coupling partners. The arenes of the formula (I) used as reactants in the present invention have a very different electronic situation compared to benzamides. It is not necessarily possible to assume a comparably good ortho-directing effect, as occurs in the reaction of benzamides and is not to be confused with the +/−I or +/−M effect in nucleophilic aromatic substitution, for the arenes of the formula (I) used as reactants in the process according to the invention. Typical examples of ortho-directing groups can be found in Eric J.-G. Anctil and Victor Snieckus in *Metal-Catalyzed Cross-Coupling Reactions*, 2nd Edition 2004, 761-813, eds.: A. de Meijere and F. Diederich, WILEY-VCH Verlag GmbH & KGaA, Weinheim (Scheme 14-2, page 762). Here, benzamides are mentioned explicitly as ortho-directing groups, but not the corresponding anilides.

In the context of the present invention, the term "halogens" includes, unless defined differently, elements selected from the group consisting of fluorine, chlorine, bromine and iodine, preference being given to using fluorine, chlorine and bromine, and particular preference to using fluorine and chlorine.

Optionally substituted groups may be mono- or polysubstituted, where the substituents in the case of polysubstitutions may be the same or different.

The alkyl groups substituted by one or more halogen atoms are, for example, selected from trifluoromethyl (—$CF_3$), difluoromethyl (—$CHF_2$), $CH_2CF_3$, $CH_2Cl$, and $CCl_2CF_3$.

Alkyl groups in the context of the present invention, unless defined differently, are linear or branched hydrocarbyl groups which may optionally have one, two or more heteroatoms selected from O, N, P and S. In addition, the inventive alkyl groups may optionally be substituted by further groups selected from —R', halogen, alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' is hydrogen or a $C_{1-12}$-alkyl group, preferably $C_{2-10}$-alkyl group, more preferably $C_{3-8}$-alkyl group, which may have one or more heteroatoms selected from N, O, P and S.

The definition $C_1$-$C_{12}$-alkyl encompasses the widest range defined herein for an alkyl group. Specifically, this definition encompasses, for example, the meanings of methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

Cycloalkyl groups in the context of the present invention, unless defined differently, are cyclic hydrocarbyl groups which may optionally have one, two or more heteroatoms selected from O, N, P and S. In addition, the inventive cycloalkyl groups may optionally be substituted by further groups selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' is hydrogen or a $C_{1-12}$-alkyl group, preferably $C_{2-10}$-alkyl group, more preferably $C_{3-8}$-alkyl group, which may have one or more heteroatoms selected from N, O, P and S.

The definition $C_3$-$C_8$-cycloalkyl encompasses the widest range defined herein for a cycloalkyl group. Specifically, this definition encompasses, for example, the meanings of cyclopropyl, cyclobutyl, cyclohexyl, cycloheptyl and cyclooctyl.

Aryl groups in the context of the present invention, unless defined differently, are aromatic hydrocarbyl groups which may have one, two or more heteroatoms selected from O, N, P and S and may optionally be substituted by further groups selected from —R', halogen, alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' is hydrogen or a $C_{1-12}$-alkyl group, preferably $C_{2-10}$-alkyl group, more preferably $C_{3-8}$-alkyl group, which may have one or more heteroatoms selected from N, O, P and S.

The definition $C_{5-18}$-aryl encompasses the widest range defined herein for an aryl group having 5 to 18 skeleton atoms, where the carbon atoms may be exchanged for heteroatoms. Specifically, this definition encompasses, for example, the meanings of cyclopentadienyl, phenyl, cycloheptatrienyl, cyclooctatetraenyl, naphthyl and anthracenyl; 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Arylalkyl groups (aralkyl groups) in the context of the present invention, unless defined differently, are alkyl groups which are substituted by aryl groups, may have a $C_{1-8}$-alkylene chain and may be selected in the aryl skeleton or the alkylene chain by one or more heteroatoms selected from O, N, P and S and may optionally be substituted by further groups selected from —R', halogen, alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' is hydrogen or a $C_{1-12}$-alkyl group, preferably $C_{2-10}$-alkyl group, more preferably $C_{3-8}$-alkyl group, which may have one or more heteroatoms selected from N, O, P and S.

The definition $C_{7-19}$-aralkyl group encompasses the widest range defined herein for an arylalkyl group having a total of 7 to 19 atoms in the skeleton and alkylene chain. Specifically, this definition encompasses, for example, the meanings of benzyl and phenylethyl.

Alkylaryl groups (alkaryl groups) in the context of the present invention, unless defined differently, are aryl groups which are substituted by alkyl groups, may have a $C_{1-8}$-alkylene chain and may be selected in the aryl skeleton or the alkylene chain by one or more heteroatoms selected from O, N, P and S and may optionally be substituted by further groups selected from —R', halogen, alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), where R' is hydrogen or a $C_{1-12}$-alkyl group, preferably $C_{2-10}$-alkyl group, more preferably $C_{3-8}$-alkyl group, which may have one or more heteroatoms selected from N, O, P and S.

The definition $C_{7-19}$-alkaryl group encompasses the widest range defined herein for an alkylaryl group having a total of 7 to 19 atoms in the skeleton and alkylene chain. Specifically, this definition encompasses, for example, the meanings of tolyl or 2,3-, 2,4-, 2,5-, 2,6-, 3,4- or 3,5-dimethylphenyl.

The alkyl, alkenyl, alkynyl, aryl, alkaryl and aralkyl groups may additionally have one or more heteroatoms which—unless defined differently—are selected from N, O, P and S. These heteroatoms replace the numbered carbon atoms. The inventive compounds may be present as mixtures of any different isomeric forms possible, especially of stereoisomers, for example E and Z isomers, threo and erythro isomers, and optical isomers, but if appropriate also of tautomers. Both the E and the Z isomers are disclosed and claimed, as are the threo and erythro isomers, and also the optical isomers, any mixtures of these isomers, and also the possible tautomeric forms.

In a preferred embodiment of the process according to the invention for preparing substituted biphenyls of the formula (III), the substituents are defined as follows:

$X^1$ and $X^2$ are each independently selected from halogen atoms;
n is selected from 0 and 1;
m is selected from 1, 2 and 3;
$R^1$ is selected from —NHR², —NR³—CO—R² and —N=CR⁴R⁵;
$R^2$-$R^5$ are each selected from hydrogen, linear or branched $C_{1-6}$-alkyl groups, —CH₂—CO—CH₃, pyrazolyl groups of the formula (IVa) and pyridyl groups of the formula (IVb)

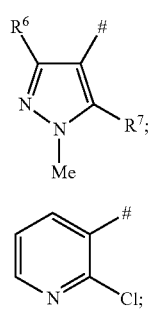

where, in the formulae (IVa) and (IVb), when $R^1$ is —NR³—CO—R², the bond marked with # is bonded to the carbonyl group in each case, $R^6$ and $R^7$ are each selected from hydrogen, halogen, a linear or branched $C_{1-6}$-alkyl group and a $C_{1-6}$-haloalkyl group having 1 to 6 halogen atoms.

In a further preferred embodiment of the process according to the invention for preparing substituted biphenyls of the formula (III), the substituents are defined as follows:

$X^1$ and $X^2$ are each independently selected from halogen atoms;
n is selected from 0 and 1;
m is selected from 1, 2 and 3;
$R^1$ is selected from —NHR² and —NR³—CO—R²;
$R^2$-$R^5$ are each selected from hydrogen, linear or branched $C_{1-6}$-alkyl groups, —CH₃—CO—CH₃, pyrazolyl groups of the formula (IVa) and pyridyl groups of the formula (IVb)

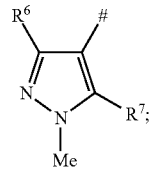

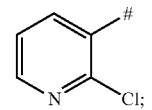

where, in the formulae (IVa) and (IVb), when $R^1$ is —NR³—CO—R², the bond marked with # is bonded to the carbonyl group in each case, $R^6$ and $R^7$ are each selected from hydrogen, halogen, a linear or branched $C_{1-6}$-alkyl group and a $C_{1-6}$-haloalkyl group having 1 to 6 halogen atoms;

In a further preferred embodiment of the process according to the invention for preparing substituted biphenyls of the formula (III), the substituents are defined as follows:

$X^1$ and $X^2$ are each independently selected from halogen atoms;
n is selected from 0 and 1;
m is selected from 1, 2 and 3;
$R^1$ is —NR³—CO—R²;
$R^2$-$R^5$ are each selected from hydrogen, linear or branched $C_{1-6}$-alkyl groups, —CH₃—CO—CH₃, pyrazolyl groups of the formula (IVa) and pyridyl groups of the formula (IVb)

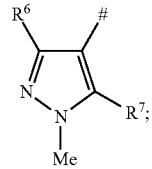

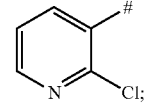

where, in the formulae (IVa) and (IVb), when $R^1$ is —NR³—CO—R², the bond marked with # is bonded to the carbonyl group in each case, $R^6$ and $R^7$ are each selected from hydrogen, halogen, a linear or branched $C_{1-6}$-alkyl group and a $C_{1-6}$-haloalkyl group having 1 to 6 halogen atoms.

In a particularly preferred embodiment of the process according to the invention for preparing substituted biphenyls of the formula (III), the substituents in formula (III) are defined as follows:

$X^1$ is 5-fluoro;
n is 1;
$X^2$ is 3,4-chloro;
m is 2;
$R^1$ is selected from —NH₂ and —NH—CO—R²;
$R^2$ is selected from methyl, —CH₂—CO—CH₃ and pyrazolyl groups of the formula (IVa)

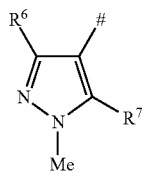

where, in the formula (IVa), when $R^1$ is —NH—CO—$R^2$, the bond marked with # is bonded to the carbonyl group in each case;
$R^6$ is difluoromethyl and
$R^7$ is hydrogen.

In a very particularly preferred embodiment of the process according to the invention for preparing substituted biphenyls of the formula (III), the substituents in formula (III) are defined as follows:
$X^1$ is 5-fluoro;
n is 1;
$X^2$ is 3,4-chloro;
m is 2;
$R^1$ is —NH—CO—$R^2$;
$R^2$ is selected from methyl, —$CH_2$—CO—$CH_3$ and pyrazolyl groups of the formula (IVa)

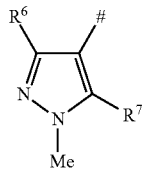

where, in the formula (IVa), when $R^1$ is —NH—CO—$R^2$, the bond marked with # is bonded to the carbonyl group in each case;
$R^6$ is difluoromethyl and
$R^7$ is hydrogen.

In a further particularly preferred embodiment of the process according to the invention for preparing substituted biphenyls of the formula (III), the substituents in formula (III) are defined as follows:
n is 0;
$X^2$ is 3,4,5-fluoro;
m is 3;
$R^1$ is selected from —$NH_2$ and —NH—CO—$R^2$;
$R^2$ is selected from methyl, —$CH_2$—CO—$CH_3$ and pyrazolyl groups of the formula (IVa)

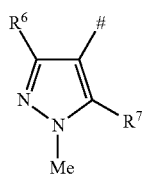

where, in the formula (IVa), when $R^1$ is —NH—CO—$R^2$, the bond marked with # is bonded to the carbonyl group;
$R^6$ is difluoromethyl and
$R^7$ is hydrogen.

In a further particularly preferred embodiment of the process according to the invention for preparing substituted biphenyls of the formula (III), the substituents in formula (III) are defined as follows:
n is 0;
$X^2$ is 3,4,5-fluoro;
m is 3;
$R^1$ is —NH—CO—$R^2$;
$R^2$ is selected from methyl, —$CH_2$—CO—$CH_3$ and pyrazolyl groups of the formula (IVa)

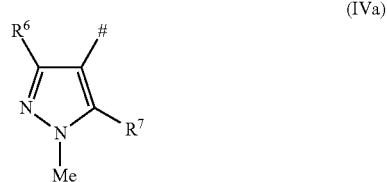

where, in the formula (IVa), when $R^1$ is —NH—CO—$R^2$, the bond marked with # is bonded to the carbonyl group;
$R^6$ is difluoromethyl and
$R^7$ is hydrogen.

In a further particularly preferred embodiment of the process according to the invention for preparing substituted biphenyls of the formula (III), the substituents in formula (III) are defined as follows:
n is 0;
$X^2$ is 4-chloro;
m is 1;
$R^1$ is selected from —$NH_2$ and —NH—CO—$R^2$;
$R^2$ is selected from methyl, —$CH_2$—CO—$CH_3$ and pyridyl groups of the formula (IVb)

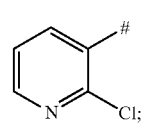

where, in the formula (IVb), when $R^1$ is —NH—CO—$R^2$, the bond marked with # is bonded to the carbonyl group.

In a further particularly preferred embodiment of the process according to the invention for preparing substituted biphenyls of the formula (III), the substituents in formula (III) are defined as follows:
n is 0;
$X^2$ is 4-chloro;
m is 1;
$R^1$ is —NH—CO—$R^2$;
$R^2$ is selected from methyl, —$CH_2$—CO—$CH_3$ and pyridyl groups of the formula (IVb)

where, in the formula (IVb), when $R^1$ is —NH—CO—$R^2$, the bond marked with # is bonded to the carbonyl group.

The arenes of the formula (I) in the context of the present invention are substituted as follows:

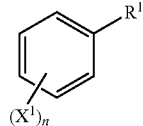
(I)

$X^1$ is independently selected from halogen atoms and linear or branched $C_{1-4}$-alkyl groups substituted by one or more halogen atoms;

n is selected from 0, 1 and 2;

$R^1$ is selected from —$NHR^2$, —$NO_2$, —$NR^3$—CO—$R^2$ and —N=$CR^4R^5$;

$R^2$-$R^5$ are selected from hydrogen, linear or branched $C_{1-12}$-alkyl groups, cyclic $C_{3-8}$-alkyl groups, —$CH_2$—CO—$CH_3$, benzyl groups, benzoyl groups, pyrazolyl groups of the formula (IVa) and pyridyl groups of the formula (IVb)

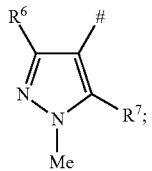
(IVa)

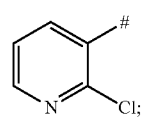
(IVb)

where, in the formulae (IVa) and (IVb), when $R^1$ is —$NR^3$—CO—$R^2$, the bond marked with # is bonded to the carbonyl group in each case, $R^6$ and $R^7$ are each selected from hydrogen, halogen, a linear or branched $C_{1-12}$-alkyl group and a $C_{1-6}$-haloalkyl group having 1 to 6 halogen atoms.

In a preferred embodiment of the present invention, the arenes of the formula (I) are substituted as follows:

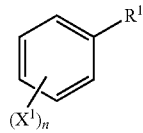
(I)

$X^1$ is independently selected from halogen atoms;

n is selected from 0, 1 and 2;

$R^1$ is selected from —$NHR^2$, —$NO_2$, —$NR^3$—CO—$R^2$ and —N=$CR^4R^5$;

$R^2$-$R^5$ are selected from hydrogen, linear or branched $C_{1-12}$-alkyl groups, cyclic $C_{3-8}$-alkyl groups, —$CH_2$—CO—$CH_3$, benzyl groups, benzoyl groups, pyrazolyl groups of the formula (IVa) and pyridyl groups of the formula (IVb)

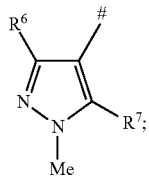
(IVa)

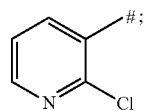
(IVb)

where, in the formulae (IVa) and (IVb), when $R^1$ is —$NR^3$—CO—$R^2$, the bond marked with # is bonded to the carbonyl group in each case, $R^6$ and $R^7$ are each selected from hydrogen, halogen, a linear or branched $C_{1-12}$-alkyl group and a $C_{1-6}$-haloalkyl group having 1 to 6 halogen atoms.

In a preferred embodiment of the present invention, the arenes of the formula (I) are substituted as follows:

(I)

$X^1$ is 4-fluoro;

n is selected from 0 and 1;

$R^1$ is selected from —$NHR^2$ and —$NR^3$—CO—$R^2$;

$R^2$-$R^5$ are selected from hydrogen, linear or branched $C_{1-12}$-alkyl groups, cyclic $C_{3-8}$-alkyl groups, —$CH_2$—CO—$CH_3$, benzyl groups, benzoyl groups, pyrazolyl groups of the formula (IVa) and pyridyl groups of the formula (IVb)

(IVa)

(IVb)

where, in the formulae (IVa) and (IVb), when $R^1$ is —$NR^3$—CO—$R^2$, the bond marked with # is bonded to the carbonyl group in each case, $R^6$ and $R^7$ are each selected from hydrogen, halogen, a linear or branched $C_{1-12}$-alkyl group and a $C_{1-6}$-haloalkyl group having 1 to 6 halogen atoms;

In a preferred embodiment of the present invention, the arenes of the formula (I) are substituted as follows:

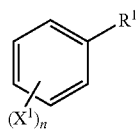

X¹ is 4-fluoro;
n is selected from 0 and 1;
$R^1$ is —$NR^3$—CO—$R^2$;
$R^2$-$R^5$ are selected from hydrogen, linear or branched $C_{1-12}$-alkyl groups, cyclic $C_{3-8}$-alkyl groups, —$CH_2$—CO—$CH_3$, benzyl groups, benzoyl groups, pyrazolyl groups of the formula (IVa) and pyridyl groups of the formula (IVb)

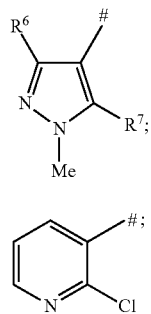

where, in the formulae (IVa) and (IVb), when $R^1$ is —$NR^3$—CO—$R^2$, the bond marked with # is bonded to the carbonyl group in each case,
$R^6$ and $R^7$ are each selected from hydrogen, halogen, a linear or branched $C_{1-12}$-alkyl group and a $C_{1-6}$-haloalkyl group having 1 to 6 halogen atoms.

In a further preferred embodiment of the invention, the arenes of the formula (I) are selected from pyrazolyl- or pyridylanilides ($R^1$=—NH—CO—$R^2$—), the pyrazolyl groups of the formula (IVa) where $R^6$=$CHF_2$ and $R^7$=hydrogen or fluorine and pyridyl groups of the formula (IVb).

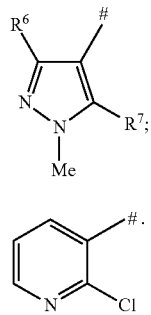

Particular preference is given to N-phenyl-3-(difluoromethyl)-1-methyl-1H-pyrazole-4-carboxamide, N-(4-fluorophenyl)-3-(difluoromethyl)-1-methyl-1H-pyrazole-4-carboxamide and N-phenyl-2-chloronicotinamide.

In a further preferred embodiment of the process according to the invention, the arenes of the formula (I) are selected from aniline, 4-fluoroaniline, acetanilide, 4-fluoroacetanilide, N-phenyl-3-oxobutanamide, N-(4-fluorophenyl)-3-oxobutanamide, N-(propan-2-ylidene)aniline, 4-fluoro-N-(propan-2-ylidene)aniline, N-phenyl-3-(difluoromethyl)-1-methyl-1H-pyrazole-4-carboxamide, N-(4-fluorophenyl)-3-(difluoromethyl)-1-methyl-1H-pyrazole-4-carboxamide and N-phenyl-2-chloronicotinamide.

In a particularly preferred embodiment of the process according to the invention, the arenes of the formula (I) are selected from aniline, 4-fluoroaniline, N-(propan-2-ylidene)aniline and 4-fluoro-N-(propan-2-ylidene)aniline, most preferably from aniline, 4-fluoroaniline.

In a further particularly preferred embodiment of the process according to the invention, the arenes of the formula (I) are selected from acetanilide, 4-fluoroacetanilide, N-phenyl-3-oxobutanamide, N-(4-fluorophenyl)-3-oxobutanamide, N-phenyl-3-(difluoromethyl)-1-methyl-1H-pyrazole-4-carboxamide, N-(4-fluorophenyl)-3-(difluoromethyl)-1-methyl-1H-pyrazole-4-carboxamide and N-phenyl-2-chloronicotinamide, most preferably from acetanilide, 4-fluoroacetanilide, N-phenyl-3-(difluoromethyl)-1-methyl-1H-pyrazole-4-carboxamide, N-(4-fluorophenyl)-3-(difluoromethyl)-1-methyl-1H-pyrazole-4-carboxamide and N-phenyl-2-chloronicotinamide.

In a further preferred embodiment of the process according to the invention, the arenes of the formula (II) are selected from 1,2-dichlorobenzene, chlorobenzene and 1,2,3-trifluorobenzene.

The arenes of the formula (II) in the context of the present invention are substituted as follows:

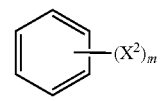

$X^2$ is selected from halogen atoms and linear or branched $C_{1-4}$-alkyl groups substituted by one or more halogen atoms;
m is selected from 1, 2, 3, 4 and 5.

In a preferred embodiment of the present invention, the arenes of the formula (II) are substituted as follows:

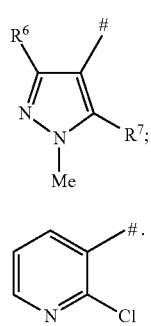

$X^2$ is selected from halogen atoms;
m is selected from 1, 2, 3, 4 and 5.

In a preferred embodiment of the present invention, the arenes of the formula (II) are substituted as follows:

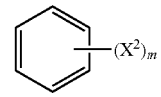

$X^2$ is selected from halogen atoms, more preferably from chlorine and fluorine;
m is selected from 1, 2 and 3, more preferably from 2 and 3.

In a particularly preferred embodiment of the present invention, the arenes of the formula (II) are selected from 1,2-dichlorobenzene, chlorobenzene and 1,2,3-trifluorobenzene.

The coupling of the arenes of the formula (I) with the arenes of the formula (II) preferably takes place in the presence of at least one solvent selected, for example, from the group consisting of water, aliphatic ethers, optionally halogenated aromatic or aliphatic hydrocarbons, alcohols, esters, aromatic or aliphatic nitriles, and dipolar aprotic solvents such as dialkyl sulphoxides, N,N-dialkylamides of aliphatic carboxylic acids or alkylated lactams.

Particular preference is given to solvents selected from the group consisting of 1,2-dichlorobenzene, chlorobenzene, 1,2,3-trifluorobenzene, THF, dioxane, diethyl ether, diglyme, methyl tert-butyl ether (MTBE), tert-amyl methyl ether (TAME), dimethyl ether (DME), 2-methyl-THF, acetonitrile, butyronitrile, toluene, xylenes, mesitylene, anisole, ethyl acetate, isopropyl acetate, methanol, ethanol, propanol, butanol, ethylene glycol, ethylene carbonate, propylene carbonate, N,N-dimethylacetamide, N,N-dimethylformamide, N-methylpyrrolidone, water and mixtures of these.

In a particularly preferred embodiment of the present invention, the arene of the formula (II) is used as the solvent. In a particularly preferred embodiment of the present invention, the solvent is selected from 1,2-dichlorobenzene, 1,2,3-trifluorobenzene and chlorobenzene.

The aryl-aryl coupling proceeds in the presence of transition metal catalysts. In principle, it is possible to use all transition metal catalysts described in the prior art in connection with aryl-aryl couplings.

Preference is given to using catalysts based on the transition metals M, where

M is selected from the metals Ni, Pd, Pt, Cu, Ag, Au, Co, Rh, Ir, Fe, Ru, Mn, Cr and Ti.

In a preferred embodiment, M is selected from Ru, Pd and Rh. In a particularly preferred embodiment, M is selected from Ru and Pd. In a very particularly preferred embodiment, M is Ru.

The transition metals M may be present in the oxidation states of −II to +VI.

The catalysts used may also be metal salts consisting of the abovementioned metals M in the form of $MY_p$ where M is selected from Ni, Pd, Pt, Cu, Ag, Au, Co, Rh, Ir, Fe, Ru, Mn, Cr and Ti, preferably from Ru, Pd and Rh, more preferably from Ru and Pd, and M is most preferably Ru;

Y is independently selected from F, Cl, Br, I, OTf, OAc, OMes, OTos, $CF_3CO_2$, $SO_4$ and acetylacetonate, preferably from Cl and OAc.

p is selected from 1, 2, 3, 4, 5 and 6, preferably from 2, 3 and 4.

The catalysts used may also be transition metal complexes of the formula $MY_pL_r$ which can be obtained by combination of the abovementioned transition metal salts $MY_p$ with ligands L, where M is selected from Ni, Pd, Pt, Cu, Ag, Au, Co, Rh, Ir, Fe, Ru, Mn, Cr and Ti, preferably from Ru, Pd and Rh, more preferably from Ru and Pd, and M is most preferably Ru;

Y is independently selected from F, Cl, Br, I, OTf, OAc, OMes, OTos, $CF_3CO_2$, $SO_4$ and acetylacetonate, preferably from Cl and OAc;

p is selected from 1, 2, 3, 4, 5 and 6, preferably from 2, 3 and 4;

L is independently selected from Cp (cyclopentadienide), Cp*(pentamethylcyclopentadienide), p-cymene, $PR'_3$ and phosphoramidate;

R' is independently selected from $C_{1-6}$-alkyl, $C_{3-5}$-cycloalkyl, $C_{6-12}$-aryl, $C_{12-24}$-biaryl and phosphinoferrocene ligands; and r is selected from 0, 1, 2, 3, 4, 5 and 6, preferably from 2, 3 and 4.

In a preferred embodiment of the present invention, the phosphinoferrocene ligands are selected from 1,1-bis-(di-tert-butylphosphino)ferrocene and pentaphenyl(di-tert-butylphosphino)ferrocene.

In a particularly preferred embodiment, the transition metal complex is of the formula $MY_pL_r$ [RhCp*Cl$_2$]$_2$.

In the course of performance of the reaction, the catalyst system (transition metal or transition metal salt and ligand) can be added together or separately. The addition is effected at room temperature or at a temperature of 30° C. to 100° C. The addition is preferably effected at room temperature. It is possible to produce the transition metal complex catalyst shortly prior to the performance separately by combination of a transition metal salt and of the ligand, or to purchase it commercially in crystalline form. Preferably, the transition metal catalysts used in the reaction are obtained in situ from at least one transition metal salt $MY_p$ and the appropriate ligands L. The transition metal salts can also be used directly, i.e. without combination with the ligands L, without any resulting reduction in the initial catalytic activity.

In a preferred embodiment of the present invention, the transition metal complex $MY_pL_r$ is obtained in situ from the transition metal salt $MY_p$ and the ligand L.

In a preferred embodiment of the present invention, the molar ratio of transition metal M to ligand L is between 4:1 and 1:50. In a particularly preferred embodiment, the molar ratio of transition metal M to ligand L is between 1:1 and 1:5. In a very particularly preferred embodiment, the molar ratio of transition metal M to ligand L is between 1:1 and 1:2.

In the process according to the invention, 0.001 to 10.0 mol %, preferably 0.01 to 5.0 mol %, more preferably 0.1 to 2.5 mol %, of the transition metal catalyst is used—based on the arene of the formula (I).

According to the present invention, the arenes (I) and (II) are coupled using at least one independently combinable oxidizing agent. In principle, it is possible to use all suitable oxidizing agents and electrochemical oxidation. In a preferred embodiment, the oxidizing agents are selected from benzoquinone, atmospheric oxygen, $O_2$, $AgNO_3$, AgOAc, $Cu(OAc)_2$, $Ag_2CO_3$, $AgSbF_6$, $K_2S_2O_8$, $H_4PMo_{11}VO_{40}$, $Cu(OTf)_2$, $Na_2S_2O_8$. In a particularly preferred embodiment, atmospheric oxygen is used as the oxidizing agent. In a further particularly preferred embodiment, $AgSbF_6$ and $Cu(OAc)_2$ are used as oxidizing agents.

In combination with the catalyst, in the process according to the invention, 0.1 to 10.0 equivalents, preferably 0.5 to 5 equivalents, more preferably 1.0 to 2.5 equivalents, of the oxidizing agent or of the independently combinable oxidizing agents—based on the arene of the formula (I)—are used. In the case of use of $AgSbF_6$ and $Cu(OAc)_2$ as oxidizing agents, 0.05-0.5, preferably 0.05-0.2, equivalent of $AgSbF_6$ and 0.5 to 5 equivalents, preferably 1.0 to 2.5, equivalents of $Cu(OAc)_2$—based on the arene of the formula (I)—are used.

According to the present invention, the arenes of the formulae (I) and (II) can be coupled using up to ten, preferably up to five, more preferably up to three, independently combinable additives. Additives may firstly be chelators which chelate over 1-3 coordination sites. Coordination sites here may be heteroatoms and multiple bonds, preferably oxygen and nitrogen atoms and double bonds. Nonlimiting examples thereof are pTsOH, AcOH, TFA, CsOPiv, PivOH. In addition, additives may also be auxiliaries which serve to release catalytic activity. Nonlimiting examples thereof are $KPF_6$, $PPh_3$, $NH_4PF_6$, $NaBF_4$.

In a preferred embodiment of the present invention, the additives are selected from pTsOH, AcOH, TFA, CsOPiv, PivOH, $KPF_6$, $PPh_3$, $NH_4PF_6$ and $NaBF_4$.

In a further preferred embodiment of the present invention, the additives are selected from pTsOH, AcOH, TFA, CsOPiv and PivOH. In a particularly preferred embodiment, the additives are selected from CsOPiv and PivOH.

In a further preferred embodiment of the present invention, the additives are selected from $KPF_6$, $PPh_3$, $NH_4PF_6$, $NaBF_4$.

In a preferred embodiment, up to five independently combinable additives are used. In a particularly preferred embodiment, up to three independently combinable additives are used.

In a preferred embodiment of the present invention, 0.01 to 10 equivalents, preferably 0.05 to 5 equivalents, more preferably 0.1 to 1.5 equivalents, of the additive or of the independently combinable additives—based on the arene of the formula (I)—are used.

According to the present invention, the arenes of the formula (I) and the arenes of the formula (II) are used in a ratio between 5:1 and 1:5, preferably in a ratio between 2:1 and 1:2 (I:II). Alternatively, however, one of the two components (I or II), preferably the arene of the formula (II), can also be used in a large excess as a solvent.

In a preferred embodiment of the present invention, the arene of the formula (I) or the arene of the formula (II), preferably the arene of the formula (II), is used in a large excess as a solvent.

The reaction is performed generally at a temperature of 20 to 200° C., preferably of 50 to 150° C., more preferably of 120 to 140° C., and at a pressure between standard pressure and 100 bar, preferably at a pressure between standard pressure and 40 bar.

In a preferred embodiment, the reaction is effected with exclusion of atmospheric oxygen under a protective gas atmosphere, for example under an argon or nitrogen atmosphere.

Because of the small amounts of catalyst, the catalyst may in most cases remain in the end product. Alternatively, however, purification of the biaryls obtained can also be effected by filtration, for example through Celite.

The example which follows serves to illustrate the process according to the invention, without any restriction thereto:

SYNTHESIS EXAMPLE

Example 1

Coupling of N-(4-fluorophenyl)acetamide with 1,2-dichlorobenzene in the presence of $[RhCp*Cl_2]_2$ 153.2 mg (1.00 mmol) of N-(4-fluorophenyl)acetamide, 15.5 mg (0.02 mmol) of $[RhCp*Cl_2]_2$, 34.4 mg (0.10 mmol) of $AgSbF_6$, 399.6 mg (2.20 mmol) of $Cu(OAc)_2$, 112.3 mg (1.10 mmol) of PivOH and 46.8 mg (0.2 mmol) of CsOPiv were initially charged with exclusion of oxygen in a baked-out Radley reaction tube, and 5.0 ml (44.4 mmol) of 1,2-dichlorobenzene were added. The reaction mixture was stirred at 130° C. for 19 hours. After the reaction had ended (HPLC monitoring), the reaction mixture was cooled to RT, filtered through a short silica gel column and eluted with EtOAc. The solvent was removed by distillation and the crude product was purified by means of preparative HPLC. This gave 134.0 mg of N-(3',4'-dichloro-5-fluorobiphenyl-2-yl)acetamide with an LC purity of 99.9% (45% yield).

The invention claimed is:

1. Process for preparing a substituted biphenyl of formula (III)

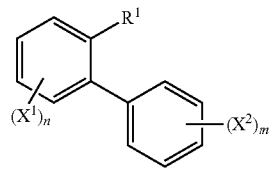

(III)

where $X^1$ and $X^2$ are each independently selected from halogen atoms;

n is selected from 0, 1 and 2;

m is selected from 1, 2, 3, 4 and 5;

$R^1$ is selected from —$NHR^2$, —$NO_2$, —$NR^3$—CO—$R^2$ and —N=$CR^4R^5$;

$R^2$-$R^5$ are each selected from hydrogen, linear or branched $C_{1-12}$-alkyl groups, cyclic $C_{3-8}$-alkyl groups, —$CH_2$—CO—$CH_3$, benzyl groups, benzoyl groups, pyrazolyl groups of formula (IVa) and pyridyl groups of the formula (IVb)

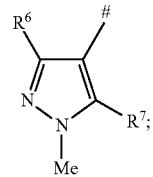

(IVa)

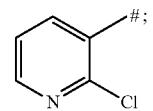

(IVb)

where, in formulae (IVa) and (IVb), when $R^1$ is —$NR^3$—CO—$R^2$, the bond marked with # is bonded to the carbonyl group in each case, $R^6$ and $R^7$ are each selected from hydrogen, halogen, a linear or branched $C_{1-12}$-alkyl group and a $C_{1-6}$-haloalkyl group having 1 to 6 halogen atoms;

comprising reacting one or more arenes of formula (I)

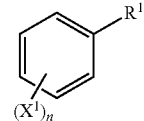

(I)

where

R$^1$, X$^1$ and n correspond to the above definitions with one or more arenes of formula (II)

(II)

[structure: benzene ring with (X$^2$)$_m$ substituent]

where

X$^2$ and m correspond to the above definitions, the reaction being performed in the presence of a transition metal catalyst, of at least one oxidizing agent, up to five additives and in a solvent.

2. Process according to claim 1, wherein

X$^1$ and X$^2$ are each independently selected from halogen atoms;

n is selected from 0 and 1;

m is selected from 1, 2 and 3;

R$^1$ is selected from —NHR$^2$, —NR$^3$—CO—R$^2$ and —N=CR$^4$R$^5$;

R$^2$-R$^5$ are each selected from hydrogen, linear or branched C$_{1-6}$-alkyl groups, —CH$_2$—CO—CH$_3$, pyrazolyl groups of formula (IVa) and pyridyl groups of formula (IVb)

(IVa)

[pyrazole structure with R$^6$, #, R$^7$, Me]

(IVb)

[pyridine structure with #, Cl]

where, in formulae (IVa) and (IVb), when R$^1$ is —NR$^3$—CO—R$^2$, the bond marked with # is bonded to the carbonyl group in each case, R$^6$ and R$^7$ are each selected from hydrogen, halogen, a linear or branched C$_{1-6}$-alkyl group and a C$_{1-6}$-haloalkyl group having 1 to 6 halogen atoms.

3. Process according to claim 1, wherein

R$^1$ is —NR$^3$—CO—R$^2$.

4. Process according to claim 1, wherein

X$^1$ in formula (III) is 5-fluoro;

n is 1;

X$^2$ in formula (III) is 3,4-chloro;

m is 2;

R$^1$ is —NH—CO—R$^2$;

R$^2$ is selected from methyl, —CH$_2$—CO—CH$_3$ and pyrazolyl groups of formula (IVa)

(IVa)

[pyrazole structure with R$^6$, #, R$^7$, Me]

where, in formula (IVa), when R$^1$ is —NH—CO—R$^2$, the bond marked with # is bonded to the carbonyl group;

R$^6$ is difluoromethyl and

R$^7$ is hydrogen.

5. Process according to claim 1, wherein n is 0;

X$^2$ in formula (III) is 3,4,5-fluoro;

m is 3;

R$^1$ is —NH—CO—R$^2$;

R$^2$ is selected from methyl, —CH$_2$—CO—CH$_3$ and pyrazolyl groups of formula (IVa)

(IVa)

[pyrazole structure with R$^6$, #, R$^7$, Me]

where, in formula (IVa), when R$^1$ is —NH—CO—R$^2$, the bond marked with # is bonded to the carbonyl group;

R$^6$ is difluoromethyl and

R$^7$ is hydrogen.

6. Process according to claim 1, wherein n is 0;

X$^2$ in formula (III) is 4-chloro;

m is 1;

R$^1$ is —NH—CO—R$^2$;

R$^2$ is selected from the group consisting of methyl, —CH$_2$—CO—CH$_3$ and pyridyl groups of formula (IVb)

(IVb)

[pyridine structure with #, Cl]

where, in formula (IVb), when R$^1$ is —NH—CO—R$^2$, the bond marked with # is bonded to the carbonyl group.

7. Process according to claim 1, wherein the arenes of formula (I) are selected from aniline, 4-fluoroaniline, acetanilide, 4-fluoroacetanilide, N-phenyl-3-oxobutanamide, N-(4-fluorophenyl)-3-oxobutanamide, N-(propan-2-ylidene)aniline, 4-fluoro-N-(propan-2-ylidene)aniline, N-phenyl-3-(difluoromethyl)-1-methyl-1H-pyrazole-4-carboxamide, N-(4-fluorophenyl)-3-(difluoromethyl)-1-methyl-1H-pyrazole-4-carboxamide and N-phenyl-2-chloronicotinamide.

8. Process according to claim 1, wherein the arenes of formula (II) are selected from 1,2-dichlorobenzene, chlorobenzene and 1,2,3-trifluorobenzene.

9. Process according to claim 1, wherein the solvent is selected from 1,2-dichlorobenzene, chlorobenzene, 1,2,3-trifluorobenzene, THF, dioxane, diethyl ether, diglyme, methyl tert-butyl ether (MTBE), tert-amyl methyl ether (TAME), dimethyl ether (DME), 2-methyl-THF, acetonitrile, butyronitrile, toluene, xylenes, mesitylene, anisole, ethyl acetate, isopropyl acetate, methanol, ethanol, propanol, butanol, ethylene glycol, ethylene carbonate, propylene carbonate, N,N-dimethylacetamide, N,N-dimethylformamide, N-methylpyrrolidone, water and mixtures thereof.

10. Process according to claim 1, wherein the metal of the transition metal catalyst is selected from Ni, Pd, Pt, Cu, Ag, Au, Co, Rh, Ir, Fe, Ru, Mn, Cr and Ti.

11. Process according to claim 1, wherein the transition metal catalyst is selected from the transition metal salts $MY_p$ where
M is selected from Ni, Pd, Pt, Cu, Ag, Au, Co, Rh, Ir, Fe, Ru, Mn, Cr and Ti;
Y is independently selected from F, Cl, Br, I, OTf, OAc, OMes, OTos, $CF_3CO_2$, $SO_4$ and acetylacetonate;
p is selected from 1, 2, 3, 4, 5 and 6.

12. Process according to claim 1, wherein the transition metal catalyst is selected from the transition metal complexes $MY_pL_r$ where
M is selected from Ni, Pd, Pt, Cu, Ag, Au, Co, Rh, Ir, Fe, Ru, Mn, Cr and Ti;
Y is independently selected from F, Cl, Br, I, OTf, OAc, OMes, OTos, $CF_3CO_2$, $SO_4$ and acetylacetonate;
p is selected from 1, 2, 3, 4, 5 and 6;
L is independently selected from Cp (cyclopentadienide), Cp*(pentamethylcyclopentadienide), p-cymene, $PR'_3$ and phosphoramidate;
R' is independently selected from $C_{1-6}$-alkyl, $C_{3-5}$-cycloalkyl, $C_{6-12}$-aryl, $C_{12-24}$-biaryl and phosphinoferrocene ligands; and
r is selected from 0, 1, 2, 3, 4, 5 and 6.

13. Process according to claim 1, wherein the at least one oxidizing agent is selected from benzoquinone, atmospheric oxygen, $O_2$, $AgNO_3$, AgOAc, $Cu(OAc)_2$, $Ag_2CO_3$, $AgSbF_6$, $K_2S_2O_8$, $H_4PMo_{11}VO_{40}$, $Cu(OTf)_2$ and $Na_2S_2O_8$.

14. Process according to claim 1, wherein the up to five additives are selected from pTsOH, AcOH, TFA, CsOPiv, PivOH, $KPF_6$, $PPh_3$, $NH_4PF_6$ and $NaBF_4$.

15. Process according to claim 1, wherein the arene of formula (I), optionally the arene of formula (II), is used in a excess as a solvent.

16. Process according to claim 1, wherein n is 0.

17. Process according to claim 1, wherein n is 1.

18. Process according to claim 3, wherein $R^2$ is a pyrazolyl groups of formula (IVa)

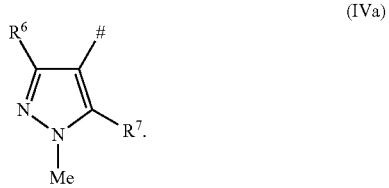

(IVa)

19. Process according to claim 18, wherein $R^6$ is difluoromethyl and $R^7$ is hydrogen.

20. Process according to claim 14, wherein one, two, three, four, or five of said additves are used.

* * * * *